(12) United States Patent
Hiemer

(10) Patent No.: US 9,149,775 B2
(45) Date of Patent: Oct. 6, 2015

(54) MIXER FOR MIXING AT LEAST TWO FLOWABLE COMPONENTS AND DISPENSING APPARATUS

(75) Inventor: Andreas Hiemer, Schübelbach (CH)

(73) Assignee: SULZER MIXPAC AG, Haag (CH)

( * ) Notice: Subject to any disclaimer, the term of this patent is extended or adjusted under 35 U.S.C. 154(b) by 0 days.

(21) Appl. No.: 13/459,409

(22) Filed: Apr. 30, 2012

(65) Prior Publication Data

US 2012/0279988 A1      Nov. 8, 2012

(30) Foreign Application Priority Data

May 2, 2011      (EP) ..................................... 11164431

(51) Int. Cl.
| | | |
|---|---|---|
| *B05C 17/005* | (2006.01) | |
| *B01F 7/00* | (2006.01) | |
| *A61C 9/00* | (2006.01) | |
| *B01F 13/00* | (2006.01) | |

(Continued)

(52) U.S. Cl.
CPC ............ *B01F 7/00216* (2013.01); *A61C 9/0026* (2013.01); *B01F 13/0023* (2013.01); *B01F 15/0087* (2013.01); *B01F 15/0206* (2013.01); *B01F 15/0256* (2013.01); *B05C 17/00516* (2013.01); *B05C 17/00553* (2013.01); *B01F 5/0602* (2013.01)

(58) Field of Classification Search
CPC ................... B05C 17/00516; B05C 17/00553; B05C 17/00586; B05C 17/00583; A61C 5/064; B67B 7/24; B01F 15/0206; A61M 5/0028; A61M 5/0036; A61M 5/0041

USPC ......... 222/80–83.5, 85–86, 88, 80–83, 145.5, 222/145.6; 215/247, 297
See application file for complete search history.

(56) References Cited

U.S. PATENT DOCUMENTS 1,550,370 A * 8/1925 Kruger ............................ 222/80
2,058,905 A * 10/1936 Moran et al. .................... 222/86

(Continued)

FOREIGN PATENT DOCUMENTS

| DE | 4316807 | 11/1994 |
| DE | 4335970 | 4/1995 |

(Continued)

OTHER PUBLICATIONS

Search Report for European Patent Application No. 11164431.6 mailed on Oct. 6, 2011.

*Primary Examiner* — Paul R Durand
*Assistant Examiner* — Charles P Cheyney
(74) *Attorney, Agent, or Firm* — Global IP Counselors, LLP

(57) ABSTRACT

An apparatus for mixing at least two flowable components having a mixer housing with an outlet opening. At least one mixing element arranged in the mixer housing having at least two separate inlet passages through which the flowable components can be introduced separately from one another. Each inlet passage is capable of being in sealing cooperation with a respective outlet passage of a storage container or a chamber. At least one of the inlet passages has an end configured to cooperate with the outlet passage as a piercing element for opening a flow connection between the storage container or the chamber and the inlet passage. The piercing element includes at least two inflow areas for the flowable components, with the two inflow areas being inclined relative to one another. A dispensing apparatus having such a mixer is furthermore provided.

17 Claims, 5 Drawing Sheets

(51) Int. Cl.
    *B01F 15/00*    (2006.01)
    *B01F 15/02*    (2006.01)
    *B01F 5/06*    (2006.01)

(56) References Cited

U.S. PATENT DOCUMENTS

| | | | |
|---|---|---|---|
| 2,587,683 A | | 3/1952 | Barry |
| 4,174,868 A | | 11/1979 | De Nardo |
| 5,242,082 A | * | 9/1993 | Giannuzzi ................ 222/82 |
| 5,566,859 A | * | 10/1996 | Willis et al. ............... 222/83.5 |
| 5,897,028 A | * | 4/1999 | Sauer ...................... 222/82 |
| 6,394,643 B1 | * | 5/2002 | Bublewitz et al. ......... 366/172.1 |
| 7,073,686 B2 | * | 7/2006 | Hanell ..................... 222/83.5 |
| 7,390,467 B2 | * | 6/2008 | Fine et al. ................ 422/256 |
| 8,147,122 B2 | * | 4/2012 | Pieroni ..................... 366/171.1 |
| 8,313,232 B2 | * | 11/2012 | Keller ...................... 366/162.3 |
| 2002/0066677 A1 | * | 6/2002 | Moscovitz ................. 206/219 |
| 2005/0161454 A1 | * | 7/2005 | Nehren et al. ............. 220/200 |
| 2007/0166660 A1 | * | 7/2007 | Peuker et al. .............. 433/89 |
| 2008/0023495 A1 | * | 1/2008 | Takayama et al. ......... 222/391 |
| 2008/0251535 A1 | * | 10/2008 | Suchan et al. ............. 222/83 |

FOREIGN PATENT DOCUMENTS

| | | |
|---|---|---|
| DE | 102007018143 | 6/2008 |
| NL | 9200318 | 9/1993 |
| WO | WO 00/21653 | 4/2000 |

* cited by examiner

MIXER FOR MIXING AT LEAST TWO FLOWABLE COMPONENTS AND DISPENSING APPARATUS

PRIORITY CLAIM

The present application claims priority to European Patent Application No. 11164431.6 filed on May 2, 2011, the disclosures of which are incorporated herein by reference.

BACKGROUND

The disclosure relates to a mixer for mixing at least two flowable components and to a dispensing apparatus in accordance with the preamble of the respective independent claim.

Static or dynamic mixers for mixing at least two components are used in a plurality of technical fields; for example in the mixing of two-component systems such as sealing compounds, two-component foams or two component adhesives or also in the dental field, for example for mixing impression materials. The individual components usually have to remain separate from one another until use and are then mixed so that hardening subsequently takes place by a chemical reaction. Such mixers are as a rule designed for single use because they can practically no longer be cleaned after hardening or after any other reaction of the components.

Such mixers are usually part of a dispensing apparatus which include cartridges or other chambers for the respective components. In use, the individual components are dispensed from the chamber by means of a plunger or by means of a drivable piston, move into the mixer, are intimately mixed there and exit the mixer through its outlet opening as a homogeneously mixed mass. There are many different designs with respect to the chambers for the components. The chambers can be designed, for example, as rigid cartridges which are inserted directly into the dispensing apparatus. In this respect, the cartridges can, for example, each have a piston as a base which is moved in the cartridge by exertion of pressure to dispense the respective component. Designs are also known in which the cartridges have very thin walls. They are then inserted into support cartridges of the dispensing apparatus and there have pressure exerted on them by a plunger or by a piston. Provision can be made in this respect that the thin-walled cartridge collapses on dispensing in the support cartridge. It is furthermore known that the chambers for the components are each designed as tubular bags which are then inserted into support cartridges and are compressed by pressure exertion for use.

As a rule, it is necessary for the storage of the individual components that they are stored in completely closed chambers to avoid any unwanted reaction with air or its components, drying or any other degradation. It is often in particular wanted to dispense with complex closure devices for the chambers with tubular bags or thin-walled cartridges as chambers for the components. It is therefore a widespread measure that the respective chamber, that is the cartridge or the tubular bag, for example, is pierced before the first use so that subsequently the corresponding component can be dispensed.

Systems are known in which an adapter is placed onto the cartridge or a holder for the tubular bag which includes a piercing device, wherein two positions are provided for the adapter, one in which the piercing device is held tight by the cartridge or by the bag respectively for storage and for transport and a second in which the piercing device penetrates into the cartridge, pierces it and thus releases the component for dispensing.

It is disadvantageous with this that the adapter is part of the disposable system and therefore has to be disposed of. As a rule, special locking devices are also required to avoid any unintentional piercing.

Other embodiments have the piercing device attached directly to the holder for the cartridge or the tubular bag respectively. If the cartridge or the tubular bag respectively is inserted and is exposed to pressure, the piercing of the wall takes place in that the latter is pressed toward the piercing device and is thereby cut open. This system is not always reliable and as a rule requires great care in storage, in transport and in handling so that the cartridge or tubular bag respectively is not unintentionally pierced.

Such systems are also known, for example from DE-196 18 693, in which the piercing devices are provided at the inlet passages of the mixer, for which purpose they are designed as obliquely cut-out pipe ends which each engage into an outlet of a chamber when the mixer is placed on and in so doing pierce the wall of the chamber. It may, however, occur in this embodiment that the pierced wall lays itself in front of the entry opening of the inlet passages and covers them at least partly, whereby the dispensing of the component is negatively influenced. This could optionally be prevented by a large penetration depth of the inlet passage into the cartridge or into the tubular bag, but the complete dispensing of the components from the cartridges or from the tubular bags respectively thereby becomes impossible, which results in uneconomic residual quantities. It is the object of the invention to comply as much as possible with this endeavor and to avoid the named disadvantages of the prior art.

Starting from this prior art, it is therefore an object of the invention to propose a mixer and a dispensing apparatus for at least two flowable components which do not have these disadvantages. A problem-free, secure storage and transport should be possible, the handling of the system should be easy and an impeding of the dispensing of the component through the pierced wall should be avoided as much as possible.

The subject matters of the disclosure satisfying these objects are characterized by the features of the respective independent claims.

SUMMARY

In accordance with the disclosure, a mixer for mixing at least two flowable components is therefore proposed having a mixer housing which has an outlet opening for the components, having at least one mixing element arranged in the mixer housing for mixing the components, having at least two separate inlet passages through which the components can be introduced into the region of the mixing element separately from one another, wherein each inlet passage is designed for sealing cooperation with a respective outlet passage of a storage container or of a chamber and wherein at least one of the inlet passages is designed at its end intended for the cooperation with the outlet passage as a piercing element for opening a flow connection between the storage container or the chamber and this inlet passage. The piercing element includes at least two inflow areas for the components, with the two inflow areas being inclined relative to one another.

Since the piercing element is shaped at the inlet passage of the mixer, the wall or the sealing of the chamber for the component in the storage chamber can only be pierced when the mixer is connected to the storage container, which usually only takes place directly before use. A secure transport, a secure storage and a simple handling are ensured by this measure. Since the piercing element moreover includes at least two mutually inclined inflow areas, it is effectively prevented that the entry of the inlet passage is clogged by the pierced wall or film. An unimpeded dispensing of the respective components is hereby made possible.

The sum of all inflow areas of an inlet passage is advantageously larger than the cross-sectional area of this inlet passage perpendicular to its longitudinal axis since the component can be dispensed particularly easily by this large total inflow area.

To make every inlet passage having a piercing element able to be flowed through by the component, it is preferably designed as a hollow body; especially preferably the inlet passage is substantially designed as a cylindrical tube.

To allow a piercing of the wall or of the sealing of the chamber for the component which is as simple a manner as possible, it is preferred that the piercing element includes at least one tip.

In accordance with a first preferred embodiment, the two inflow areas contact one another at a common connection line.

In another preferred embodiment, the two inflow areas are separated by a bar.

The bar preferably extends perpendicular to the longitudinal axis of the inlet passage.

Since this bar represents a particularly stable structure, it is advantageous if the bar has at least one tip.

The mixer can be designed as a dynamic mixer having a rotatable mixing element, that is the mixing element is rotated for mixing the components. The mixer can naturally also be designed in a manner known per se as a static mixer, that is the mixing element or the mixing elements does or do not move, but rather the mixing of the components takes place by a multiple separation of the component flows into part flows and a multiple combining of these part flows, with here the mixing energy only originating from the flowing components.

In accordance with an embodiment, precisely one inlet passage in the mixer has one piercing element; the other inlet passage or passages is or are designed without a piercing element.

Furthermore, a dispensing apparatus is proposed by the invention for dispensing at least two flowable components having a storage container for receiving one respective chamber for each component, wherein the storage container has at least one outlet passage for one of the components as well as having a mixer for mixing the components. The mixer is designed in accordance with the invention.

In an embodiment, the storage container has a shoulder part which receives one respective end of each of the chambers, wherein the at least one outlet passage is provided at the shoulder part and projects as a stub on the side of the shoulder part remote from the chambers, wherein the inlet passage of the mixer provided with the piercing element engages into the at least one outlet passage of the shoulder part and is dimensioned so that each piercing element can project up to a penetration depth into the chamber in the operating state.

To allow an emptying of the chambers in as complete a manner as possible, the penetration depth amounts to at most 50%, preferably at most 33%, of the inner extent of the inlet passage.

At least one component, namely that into which the piercing element penetrates, is designed as a tubular bag whose wall can be pierced by the piercing element. It is, however, also possible that the chamber is designed as a cartridge, in particular as a thin-walled or collapsible cartridge. It is furthermore possible that the chamber has a closure membrane or closure film so that the piercing element does not pierce the wall of the chamber, but rather this closure point.

The dispensing apparatus preferably has at least one piston or at least one plunger for dispensing the components from the chambers.

It is advantageous with respect to a particularly simple and cost-effective manufacture if the mixer housing and the mixing element are injection molded, preferably from a thermoplastic.

Further advantageous measures and embodiments of the disclosure result from the dependent claims.

Additional features and advantages are described herein, and will be apparent from the following Detailed Description and the figures.

BRIEF DESCRIPTION OF THE FIGURES

The disclosure will be explained in more detail in the following with reference to embodiments and to the drawing. There are shown in the schematic drawing, partly in section.

DETAILED DESCRIPTION

Figure 1:
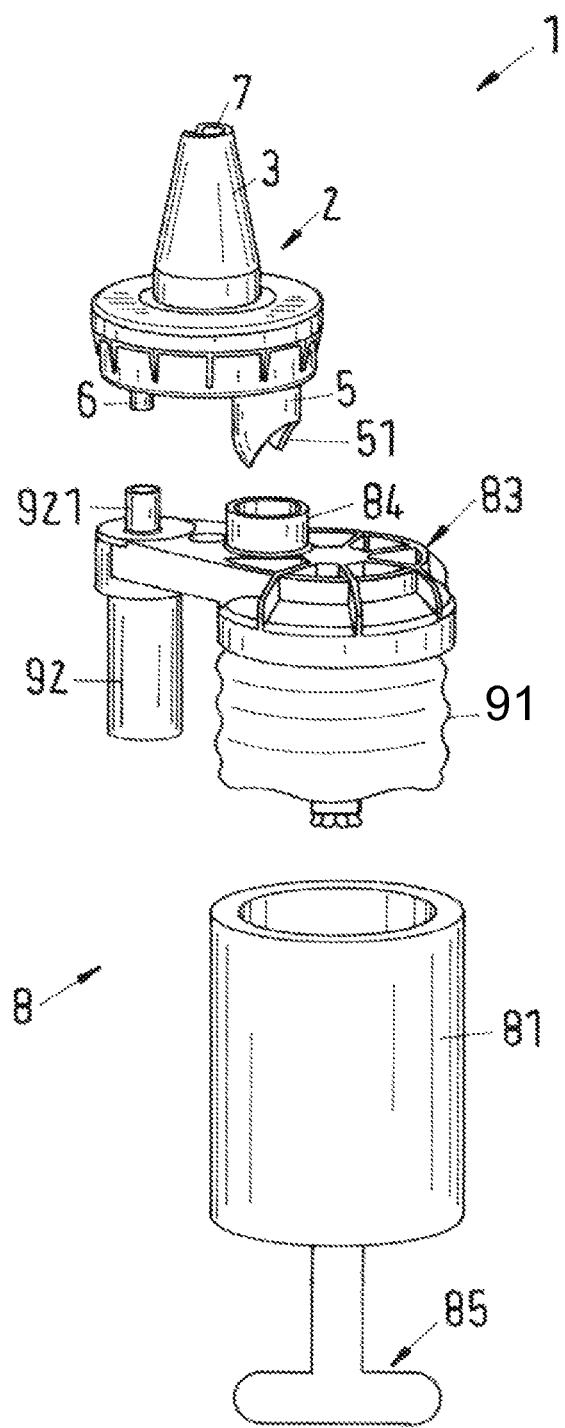
FIG. 1 is a perspective, partly schematic exploded view of an embodiment of a dispensing apparatus in accordance with the invention.
Figure 2:
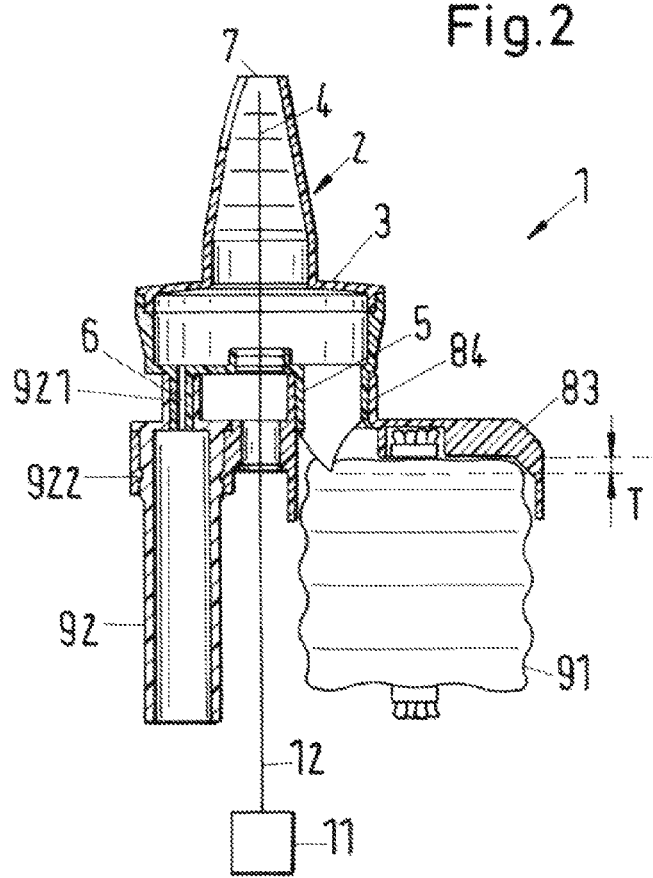
FIG. 2 a sectional view of the embodiment of FIG. 1.

FIG. 1 shows a perspective, partly schematic exploded view of major parts of an embodiment of a dispensing apparatus in accordance with the disclosure which is designated as a whole by the reference numeral 1 and includes an embodiment of a mixer in accordance with the invention which is designated as a whole by the reference numeral 2. FIG. 2 shows the embodiment in a partly schematic longitudinal sectional representation. This embodiment is designed for the dispensing or mixing of two flowable components. It is understood that the dispensing apparatus 1 or the mixer 2 can also be designed for more than two flowable components.

The mixer 2, which is here designed as a dynamic mixer, includes a mixer housing 3 in which at least one mixing element 4 is provided which is only indicated schematically in FIG. 2. This mixing element 4 serves for mixing the components. The mixer 2 includes two separate inlet passages, namely a first inlet passage 5 and a second inlet passage 6 through which the components can be introduced into the mixer 2 separately from one another and each move into the region of the mixing element 4 which then intimately mixes the two components. Finally, the mixed components exit though an outlet opening 7 of the mixer 2 and can be applied.

The components to be mixed are each provided in a chamber 91, 92 in which the components are stored and transported. Generally, all variants known per se are suitable as chambers 91, 92 for the components. The chambers 91, 92 can thus each be designed as a stable, standable cartridge which also maintains the outer shape on emptying. In this respect, the cartridge base can be formed by a piston which is moved inwardly into the cartridge in a manner known per se in the longitudinal direction by means of a plunger for emptying the cartridge. The chambers 91, 92 can also be realized by thin-walled cartridges which are inserted in a known manner into support cartridges and are, for example, collapsible for dispensing. This collapsing can work, for example, in a similar manner as with a bellows. It is furthermore possible that the chambers 91, 92 are designed as tubular bags which are then compressed in a support cartridge for dispensing. All combinations of these designs are naturally also possible for the chambers 91, 92.

In the embodiment shown here, the first chamber 91 for the first component is designed as a tubular bag and the second chamber 92 for the second component as a thick-walled—in the sense of non-collapsible—cartridge.

The dispensing apparatus 1 furthermore includes a storage container 8 which receives the two chambers 91 and 92. In this embodiment, the storage container 8 includes a support cartridge 81 (not shown in FIG. 2) into which the chamber 91, designed as a tubular bag, for the first component is inserted. Since the second chamber 92 is designed as a rigid cartridge, it does not require a support cartridge and can, for example, be inserted into a guide of the storage container 8, not shown.

The storage container 8 furthermore includes a shoulder part 83 which receives one respective end of each of the chambers 91, 92. An outlet passage 84 is furthermore provided at the shoulder part 83 and projects as a stub on the side of the shoulder part 83 remote from the chambers 91, 92. The shoulder part 83 is preferably manufactured in an injection molding method.

In the embodiment described here, the chamber 92 for the second component is designed as a cartridge which is provided with an outlet stub 921 which serves as an outlet passage for the second component. The outlet stub is provided, for example for storage and transport, with a closure cap which is removed, for example broken away, before the chamber 92 formed as a cartridge is inserted into the storage container 8. The outlet stub 921 then projects through an opening in the shoulder part 83 axially parallel to the outlet passage 84 and can receive one of the inlet passages 6 of the mixer 2.

It is naturally also possible that the second component is likewise provided in a tubular bag. It is understood that in such cases a second outlet passage is provided at the shoulder part 83 which replaces the outlet stub 921.

For dispensing the components, the dispensing apparatus 1 includes a piston or a plunger 85 which is only indicated in FIG. 1 for the first component in the support cartridge 81. It is understood that such a piston or plunger is also provided in an analog manner for the second chamber 92. It is possible in this manner that the piston is a component of the first or second chamber 91 or 92—is, for example, integrated into the cartridge which forms the second chamber 92. The piston can also be integrated into the support cartridge 81. These pistons are then moved upwardly in accordance with the illustration for dispensing the components, with the forward movement being caused by the plunger 85 which is driven manually or mechanically.

In the case of a dynamic mixer 2—as in the embodiment shown here—the dispensing apparatus 1 includes a drive 11 (FIG. 2) which sets the mixing element 4 of the mixer 2 into rotation via a shaft 12. The shaft 12 extends between the two chambers 91, 92 through an opening in the shoulder part 83 up to and into the mixer 2.

Figure 3:
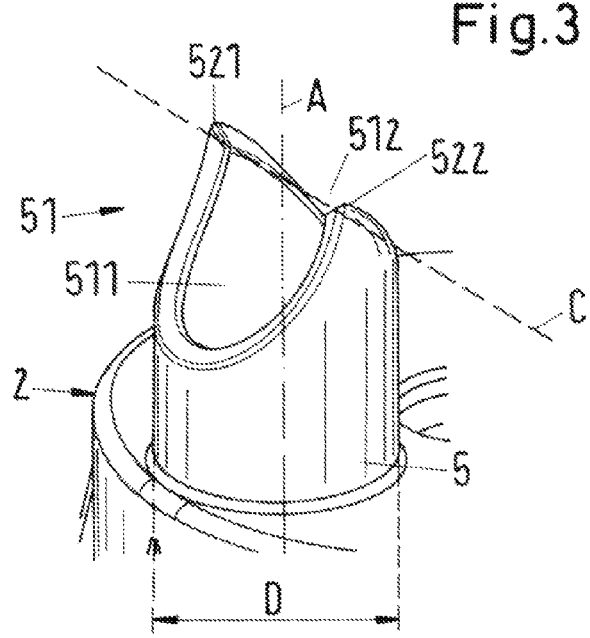
FIG. 3 is a perspective view of an inlet passage according to an embodiment of the mixer.

In accordance with the invention, at least one of the inlet passages, here the first inlet passage 5, is designed at its end intended for the cooperation with the outlet passage 84 as a piercing element 51 which serves for the opening of a flow connection between the first chamber 91 and this first inlet passage 5. In FIG. 3, the first inlet passage 5 of the embodiment of FIG. 1 and FIG. 2 is again shown perspectively. The first inlet passage 5 is substantially designed as a cylindrical tube having an inner diameter D whose end forms the piercing element 51. In accordance with the invention, the piercing element 51 has two inflow areas 511 and 512 which are inclined relative to one another and through which the first component can flow into the first inlet passage 5 from the chamber 91.

In the embodiment described here, two tips 521 and 522 are provided in the wall of the inlet passage 5 from which the wall extends cut obliquely to the longitudinal axis A on both sides, and indeed downwardly in accordance with the illustration (FIG. 3) at both sides of the tips 521 and 522. The tips 521, 522 are dispose diametrically opposite one another. The contour of the wall thus in each case substantially forms a U whose limbs each end in the tips 521 and 522 on both sides of the tips 521 and 522. As can best be seen from FIG. 1, the limbs of the two Us are each curved so that the area bounded by the U is arched in each case.

The area bounded by the one U and an imaginary connection line C (FIG. 3) between the tips 521, 522 here forms the first inflow area 511; the area bounded by the other U and the imaginary line C forms the second inflow area 512. The two inflow areas 511 and 512 thus extend inclined relative to one another and contact one another at the imaginary connection line C. As already mentioned, the two inflow areas 511 and 512 are each arched, with it having been proved advantageous if the one of the inflow areas 511, 512 is designed as concave and the other of the two inflow areas 511, 512 as convex.

For the operation of the dispensing apparatus 1 in accordance with the invention, the first chamber 91 together with the support chamber 81 and the second chamber 92 are inserted into the storage container 8 so that a respective end is received in the shoulder part 83 (see FIG. 2). If preset, the closure of the chamber 92 is previously removed. The chamber 92 provided with the outlet stub 91 and designed as a cartridge is held in the shoulder part 83 by means of a latch connection 922. The storage chamber 8 is closed and the plunger or plungers 85 or the piston or pistons are placed at the end of the chambers 91, 92 remote from the shoulder part 83.

The mixer 2 is now placed onto the shoulder part 83; in so doing, the first inlet passage 5 engages into the outlet passage 84 and the second inlet passage 6 engages into the outlet stub 921, with the inlet passages 5, 6 being designed so that they each cooperate sealingly with the outlet passage 84 or with the outlet stub 921 respectively.

On the placing of the mixer 2 onto the shoulder part 83, the piercing element 51 of the first inlet passage 5 pierces the wall of the first chamber 91 and penetrates up to a penetration depth T into the chamber 91.

It is alternatively possible that the wall of the chamber 91 is only pressed toward the piercing element and is penetrated by it on an exertion of pressure onto the first chamber 91 by means of the piston or plunger 85.

It is efficiently avoided due to the two inflow areas 511 and 512 inclined with respect to one another that on or after the piercing of the wall of the chamber 91 or of a membrane or film in the chamber 91 provided for opening, parts of the wall or of the membrane or of the film are pushed in front of the first inlet passage 5 so that the dispensing of the first component from the chamber 91 is substantially impeded.

It has proven to be advantageous in this respect if the sum of all inflow areas 511, 512 is larger than the cross-sectional area of this inlet passage 5 which is here defined by the inner diameter D. This geometrical condition can in particular be realized in that at least one of the inflow areas 511, 512 extends obliquely and not perpendicular to the longitudinal axis A.

The geometry of the piercing element 51 also makes it possible that the inlet passage 5 can be dimensioned with respect to its length such that the maximum penetration depth into the chamber 91 is small. It is thus possible, for example, to set the penetration depth T so that it amounts at most to 50%, preferably at most to 33%, of the inner extent of the inlet passage 5. In the cylindrical inlet passage 5 described here, the inner extent is the inner diameter D. Such a small penetration depth T is advantageous because an emptying of the chamber 91 is thereby made possible which is as complete as possible.

Further advantageous embodiments for the first inlet passage 5 or for the piercing element 51 respectively will now be explained in the following with reference to FIGS. 4-9 with an exemplary character. In this respect, parts which are the same or equivalent in function are designated by the same reference numerals as in FIG. 3. FIG. 4 to FIG. 9 each show a perspective representation of the inlet passage 5 with the piercing element 51.

Figure 4:
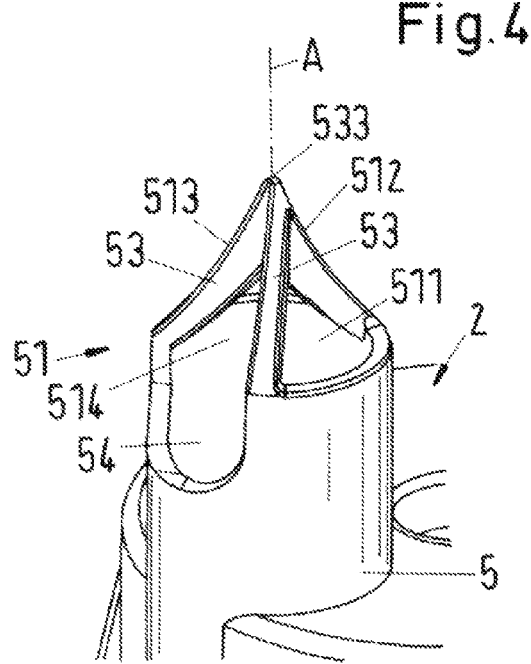
FIG. 4 is a perspective view of an inlet passage according to an embodiment of the mixer.

In the embodiment in accordance with FIG. 4, a central tip 523 is provided which is arranged on the longitudinal axis A of the inlet passage 5. Four struts 53 extend from this central tip 523, inclined with respect to the longitudinal axis A, downwardly in accordance with the representation and each end on the wall of the inlet passage 5 cut perpendicular to the longitudinal axis. In this respect, the ends are preferably distributed equidistantly over the periphery of the wall. In addition, a U-shaped cut-out 54 is provided in the cylindrical wall. To facilitate the piercing procedure, the four struts 53 can be designed twisted in each case with respect to their respective center axis. In this embodiment, four inflow areas 511, 512, 513, 514 are provided in each case between two adjacent struts 53 and the further inflow area 54 which is formed by the U-shaped cut-out.

Figure 5:
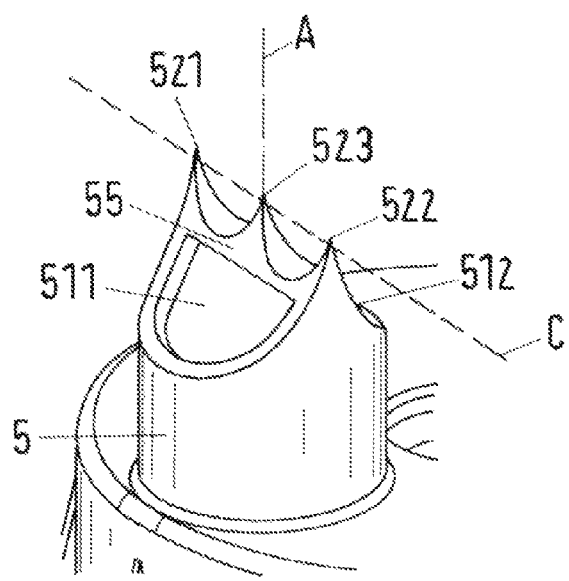
FIG. 5 is a perspective view of an inlet passage according to an embodiment of the mixer.

In the embodiment in accordance with FIG. 5, in a similar manner as with the embodiment in accordance with FIG. 3, two tips 521 and 522 are provided in the wall of the inlet passage 5 which are diametrically opposed to one another and from which the wall of the inlet passage 5 extends at both sides cut obliquely to the longitudinal axis A. The tips 521 and 522 are, however, designed as even more acute than in the embodiment in accordance with FIG. 3. In addition, in the embodiment in accordance with FIG. 5, the two tips 521 and 522 are connected by a bar 55 which extends perpendicular to the longitudinal axis A. A further central tip 523 which lies on the longitudinal axis A is provided on this bar 55. The two inflow areas 511 and 512 are separated from one another by the bar 55 in this embodiment.

Figure 6:
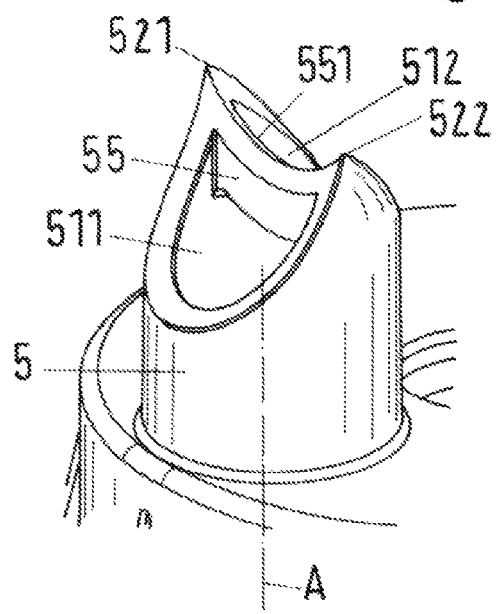
FIG. 6 is a perspective view of an inlet passage according to an embodiment of the mixer.

The embodiment in accordance with FIG. 6 is similar to the embodiment of FIG. 3, but in the embodiment in accordance with FIG. 6 the two tips 521 and 523 are connected by a bar 55 which is designed with a concave curvature here. The lateral end of the bar 55 at the top in accordance with the illustration tapers in the direction of the longitudinal axis A so that a cutting edge 551 is formed here.

Figure 7:
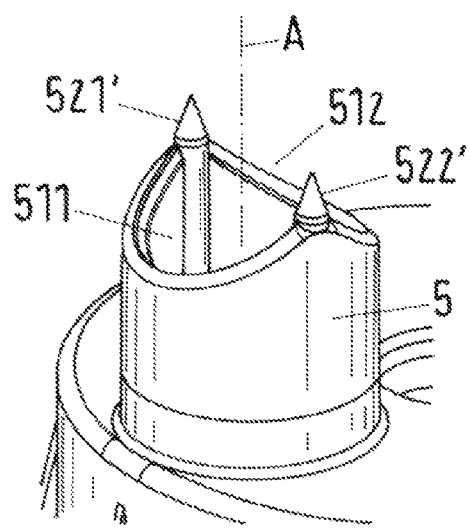
FIG. 7 is a perspective view of an inlet passage according to an embodiment of the mixer.

The embodiment in accordance with FIG. 7 is also similar to that in accordance with FIG. 3, but in the embodiment in accordance with FIG. 7 the two diametrically opposed tips 521' and 522' are each provided as isolated tips on the wall of the inlet passage 5. Both tips 521' mad 522' are each designed as conical tips 521' and 522'.

Figure 8:
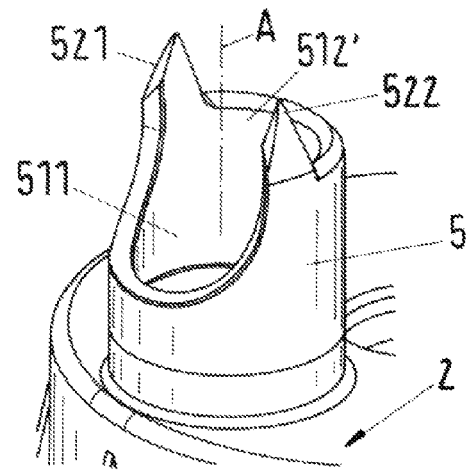
FIG. 8 is a 5 is a perspective view of an inlet passage according to an embodiment of the mixer.

FIG. 8 shows a further embodiment which is in turn similar to that in accordance with FIG. 3. However, in the embodiment in accordance with FIG. 8, the wall of the inlet passage 5 is only cut at one side of the two tips 521 and 522 obliquely to the longitudinal axis A so that the U-shaped and arched inflow area 511 results here. On the other side of the tips 521 and 522, the wall of the inlet passage 5 is cut perpendicular to the longitudinal axis A so that the associated inflow area 512' lies substantially perpendicular to the longitudinal axis A. The lateral boundaries of the two tips 521 and 522 are each cut obliquely so that each tip 521, 522 is designed in a manner similar to a tooth with a substantially triangular profile.

Figure 9:
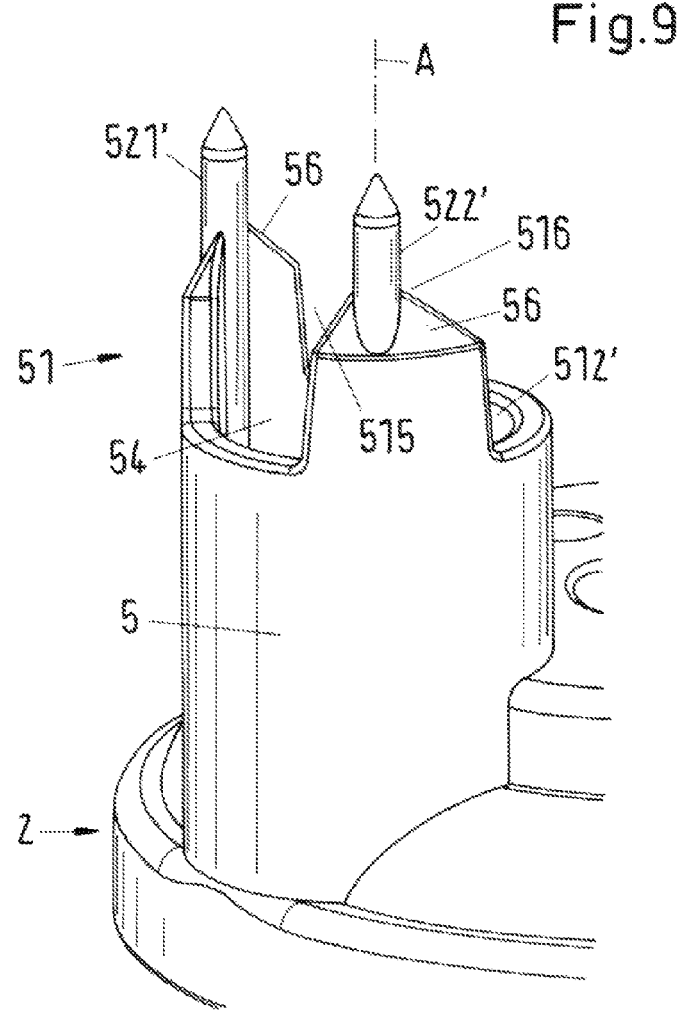
FIG. 9 is 5 is a perspective view of an inlet passage according to an embodiment of the mixer.

FIG. 9 shows an embodiment in which in a manner similar to the embodiment in accordance with FIG. 7, two isolated tips 521' and 522' are provided on the wall of the inlet passage 5 which are each designed in the manner of a column and have a conical tip. A U-shaped cut-out 54 which forms one of the inflow areas is provided in the wall of the inlet passage 5 between the two columns 521' and 522' on the one side. On the other side between the two columns 521' and 522', the wall of the inlet passage 5 has a region which is cut perpendicular to the longitudinal axis A so that an inflow area 512 is bounded thereby which extends perpendicular to the longitudinal axis A. In addition, a respective substantially triangular wall section 56 which extends inwardly inclined is provided around the columns 521' and 522'. A respective further inflow area 515 and 516 is defined at both sides of the two columns 521' and 522' by these two wall sections 56.

It is understood that the individual embodiment features which are explained with reference to FIGS. 3-9 can also be respectively combined with one another.

In the embodiment of the dispensing apparatus 1 described here, reference has been made to the application case that only one of the two components is provided in a chamber 91 which has to be opened before the use by means of the piercing element 51, whereas the other component is present in a chamber 92 designed as a cartridge which is opened, for example, by breaking away a closure or by unscrewing a cap. This application case is realized, for example, when an adhesive is provided as a first component in the first chamber 91, which is designed as a tubular bag and the second chamber 92 contains a booster as the second component which is mixed with the adhesive for faster hardening.

It is understood that the invention is naturally also suitable for such applications in which both components—or more components—are provided in chambers which are designed as tubular bags or in such chambers whose outlet is closed by a membrane, a film or another kind of sealing. In such cases, each inlet passage of the mixer which cooperates with such a chamber is provided at its respective end with a piercing element 51.

It is also understood that the piercing elements provided at different inlet passages can be designed the same or also differently.

Furthermore, the invention is naturally also suitable for such embodiments in which the mixer 2 is designed as a static mixer. One or more inlet passages for the components to be mixed can also be provided with the piercing elements in static mixers.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A mixer for mixing at least two flowable components, the mixer comprising:
   a mixer housing having an outlet opening;
   at least one mixing element arranged in the mixer housing; and
   at least two inlet passages in the mixer through which the at least two flowable components are introduced separately from one another into a region of the mixer element, each inlet passage configured as a cylindrical tube that sealingly cooperates with one respective outlet passage of a storage container or a chamber;
   wherein at least one of the at least two inlet passages is a cylindrical tube with a first end formed integrally with the mixer housing and a second end that cooperates with the outlet passage as a piercing element for opening a flow connection between the one of the storage container or the chamber and the inlet passage, the piercing element further comprising at least two inflow areas for one of the at least two flowable components,
   wherein the at least two inflow areas are inclined relative to one another,
   wherein the at least one chamber comprises an element selected from the group consisting of: a tubular bag, a cartridge, a closure membrane, and a closure film, and wherein the piercing element is configured to pierce the element to open the flow connection, and
   wherein the piercing element comprises two diametrically opposed tips on a wall of the inlet passage, each of the diametrically opposed tips comprising a column having a conical end.

2. The mixer of claim 1, wherein a sum of the at least two inflow areas is larger than a cross-sectional area of the inlet passage perpendicular to its longitudinal axis.

3. The mixer of claim 1, wherein the at least two inflow areas contact one another at a common connection line.

4. The mixer of claim 1, wherein the at least two inflow areas are separated by a bar.

5. The mixer of claim 4, wherein the bar extends perpendicularly to a longitudinal axis of the inlet passage.

6. The mixer of claim 4, wherein the bar has at least one tip.

7. The mixer of claim 1, wherein the mixer is a dynamic mixer further comprising a rotatable mixing element.

8. An apparatus for dispensing at least two flowable components comprising:
   the mixer of claim 1; and
   a storage container for receiving one respective chamber for each component, the storage container having at least one outlet passage for one of the components and a shoulder part which receives one respective end of each of the chambers,
   wherein the at least one outlet passage is provided at the shoulder part and projects as a stub on the side of the shoulder part remote from the chambers,
   wherein the piercing element of the mixer engages into the at least one outlet passage, and
   wherein the inlet passage of the mixer is dimensioned so the piercing element can penetrate up to a penetration depth into the chamber in an operating state.

9. The apparatus of claim 8, wherein the penetration depth amounts to at most 50% of an inner extent of the inlet passage.

10. The apparatus of claim 8, wherein at least one chamber configured as a tubular bag whose wall is capable of being pierced by the piercing element.

11. The apparatus claim 8, having at least one of a piston and plunger for dispensing the components from the chambers.

12. The mixer of claim 1, wherein at least one of the inflow areas extends obliquely to a longitudinal axis of the inlet passage.

13. The mixer of claim 1, wherein the piercing element comprises two tips disposed diametrically opposite one another.

14. The mixer of claim 1, wherein a wall of the inlet passage is cut obliquely to a longitudinal axis of the inlet passage to form at least one of the inflow areas.

15. The apparatus of claim 8, wherein the penetration depth amounts to at most 33% of an inner extent of the inlet passage.

16. The mixer of claim 1, wherein a first one of the at least two inflow areas is concave and a second one of the at least two inflow areas is convex.

17. The mixer of claim 1, wherein at least one of the at least two inflow areas is arched.

* * * * *